(12) United States Patent
Okuma et al.

(10) Patent No.: US 9,976,132 B2
(45) Date of Patent: May 22, 2018

(54) THERMOSTABLE CELLOBIOHYDROLASE

(71) Applicant: HONDA MOTOR CO., LTD., Minato-Ku, Tokyo (JP)

(72) Inventors: Jiro Okuma, Wako (JP); Migiwa Suda, Wako (JP); Asuka Yamaguchi, Wako (JP); Yoshitsugu Hirose, Wako (JP); Yasuhiro Kondo, Wako (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days. days.

(21) Appl. No.: 14/964,980

(22) Filed: Dec. 10, 2015

(65) Prior Publication Data
US 2016/0168549 A1 Jun. 16, 2016

(30) Foreign Application Priority Data

Dec. 12, 2014 (JP) ................. 2014-252068

(51) Int. Cl.
```
C12N 9/42      (2006.01)
C12P 19/14     (2006.01)
C12P 19/12     (2006.01)
C12N 9/24      (2006.01)
C12P 19/02     (2006.01)
```

(52) U.S. Cl.
CPC ......... *C12N 9/2434* (2013.01); *C12N 9/2437* (2013.01); *C12N 9/2482* (2013.01); *C12P 19/02* (2013.01); *C12P 19/14* (2013.01); *C12Y 302/01004* (2013.01); *C12Y 302/01008* (2013.01); *C12Y 302/01176* (2013.01)

(58) Field of Classification Search
None
See application file for complete search history.

(56) References Cited

FOREIGN PATENT DOCUMENTS

WO    2014/157492 A1    10/2014

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession D9TFI3. Oct. 5, 2010. Alignment to Seq ID No. 1.*
Accession D9TFI3. Oct. 5, 2010. Alignment to Seq ID No. 2.*
U.S. Appl. No. 15/063,941 Alignment to Seq ID No. 1 (2016).*
U.S. Appl. No. 15/063,941 Alignment to Seq ID No. 2 (2016).*
Boisset et al., "Imaging the Enzymatic Digestion of Bacterial Cellulose Ribbons Reveals the Endo Character of the Cellobiohydrolase Cel6A from Humicola insolens and its Mode of Synergy with Cellobiohydrolase Cel7A", Applied and Environmental Microbiology, 2000, vol. 66, pp. 1444-1452.
Ganju et al, "Purification and characterization of two cellobiohydrolases from *Chaetomium thermophile* var. coprophile", Biochimica et Biophysica Acta,1989, vol. 993, pp. 266-274.
Hong et al., "Cloning of a gene encoding thermostable cellobiohydrolase from Thermoascus aurantiacus and its expression in yeast", Applied Microbiology and Biotechnology, 2003, vol. 63, pp. 42-50.
Irwin et al., "Cloning, expression and characterization of a Family 48 exocellulase, Cel48A, from Thermobifida fusca", European Journal of Biochemistry, 2000, vol. 267, pp. 4988-4997.
Quinlan et al., "Pyrobayes: an improved base caller for SNP discovery in pyrosequences", Nature Methods, 2008, vol. 5, pp. 179-181.
Hoff et al., "Orphelia: predicting genes in metagenomic sequencing reads", Nucleic Acids Research Database, 2009,37 (Web Server issue: W101-W105).
Finn et al., "The Pfam protein families database", Nucleic Acids Research, 2010, vol. 38, pp. D211-D222, Helsinki, Finland.
Durbin et al., 'Biological sequence analysis: probabilistic models of proteins and nucleic acids', 1998, Cambridge University Press.
Yeoman, et al. "Thermostable Enzymes as Biocatalysts in the Biofuel Industry", Advances in Applied Microbiology, Jan. 1, 2010, pp. 1-55, vol. 70, ISSN: 0065-2164, Elsevier Inc., Academic Press, United States.
Bronnenmeier et al., "Cellulose hydrolysis by a highly thermostable endo-1, 4-beta-glucanase (Avicelase I) from Clostridium stercorarium", Enzyme Microbial Technology, Jun. 1, 1990, pp. 431-436, vol. 12, No. 6, ISSN: 0141-0229, Butterworth Publishers, Stoneham, Massachusetts, United States.
Izquierdo, et al. "Diversity of Bacteria and Glycosyl Hydrolase Family 48 Genes in Cellulolytic Consortia Enriched from Thermophilic Biocompost", Applied and Environmental Microbiology, Jun. 1, 2010, pp. 3545-3553, vol. 76, No. 11, ISSN: 0099-2240.
Riedel et al., "Synergistic interaction of the Clostridium stercorarium cellusases Avicelase I (CelY) in the degradation of microcrystalline cellulose", FEMS Microbiology Letters, 1997, pp. 239-243, vol. 147, No. 2, ISSN: 0378-1097, Elsevier Science B.V.
Search Report to corresponding European Application No. 15199324.3 mailed Apr. 19, 2016.
Riedel et al., "Synergistic interaction of the Clostridium stercorarium cellusases Avicelase I (CelZ) and Avicelase II (CelY) in the degradation of microcrystalline cellulose", FEMS Microbiology Letters, 1997, pp. 239-243, vol. 147, No. 2, ISSN: 0378-1097, Elsevier Science B.V.

(Continued)

*Primary Examiner* — Christian Fronda
(74) *Attorney, Agent, or Firm* — Carrier Blackman & Associates, P.C.; Joseph P. Carrier; Fulchand P. Shende

(57) ABSTRACT

A thermostable cellobiohydrolase, having a cellobiohydrolase catalytic domain including: (A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of phosphoric acid swollen Avicel at least under conditions of 75° C. and pH 5, or (C) a polypeptide including an amino acid sequence having 60% or greater sequence identity with the amino acid sequence represented by SEQ ID NO: 1 or 2, and having hydrolysis activity against a substrate of phosphoric acid swollen Avicel at least under conditions of 75° C. and pH 5.

2 Claims, 5 Drawing Sheets

(56) References Cited

OTHER PUBLICATIONS

Jikken-Igaku online, Bio-keywords, section of "Sequence Similarity", Internet <URL: https://www.yodosha.co.jp/iikkenigaku/keyword/2456.html>, retrieved on Sep. 27, 2017.
Office Action, dated Sep. 26, 2017, issued in the corresponding Japanese Patent Application No. JP 2014-252068.

\* cited by examiner

FIG. 1

```
AR15G-2       1  MIKFQKSVLTWLCIILPIPTALFSADVNLSAEKQSEKTMYKEEMQEIRDPNNGYLSNEGIPYHSIEK  70
C. stercorarium  1                                       YKQRFEEMEELIDPSNGYFSSHGIPYHAVET  32

AR15G-2      71  IIEAHDYGIHSISEAMSELIMIEALAYEIKDAWSVEEKSNEVMEKVFIPDKKTEQPN--MDAWNFDKPA 138
C. stercorarium 33  IMEAPDYGHLTISEAMSYMIEALGKEIIGDFSYIMKAMETIEKVFIR-TEQDQPNRSMAGMNPAKPA 101

AR15G-2     139  SVYPEYDDPYKMEAGVIYEEPVGVDPLD-DVTAKYG-HAMYLMIHIEIPDVDDMYGESKYSGGRKRAVLVML 206
C. stercorarium 102 TMAPMEEPSMVPSQLDFSAPVGIDDIYNELVSTVGTNTIMGMIHMILIDVDDMYGIGRRADRISSPAYIIT 171

AR15G-2     207  FQRGPNESTMEIIPHPSIENYINKPQ-GEVDLEVQSN--ANQMRYMISAPDAEARVAQAFVWAEEFARQK 273
C. stercorarium 172 FQRGSQESVMEIIPQCWDDLIIGGRNGELDIEVVGDSQYSAQFKVIMAPDDADARAIQATYMIENQMAKEHG 241

AR15G-2     274  WGKISDVRLMYEMGDANRVCLIFDKYHIGAGRITPGKGVDSCIMIISMYVAMGAALNEKMAMRIIGGSQA 343
C. stercorarium 242 VN--LSQVVKLASRMGDYIRVAMPDKYRKIGDSKQAGTGVDAAIVMLSMYVAMGGITADMIAMIEGGSHV 310

AR15G-2     344  ICGVQNPLGAYYIS-------KIGVQDDIDKSIKRQTEILIEFCQAVNGAIGGGVINDMD------RPNGP 399
C. stercorarium 311 HAGVQNPITAWIANDPEFKPESPNGANDWAASIEROLEFYQWLSAEGANAGGATNSYKGRYETLPAGI 380

AR15G-2     400  --FYGMHVSQHPVYIDPPSNIMISGWQYTLMERNFQVILASGDKKAFKICEKILYEMALKEPMKIT-DNDIE 466
C. stercorarium 381 STYGNAVEEIPVVIDPGSNIHFGFQANTQRVAEVYMLTGDTRAEQLIDKMV-DNIKSVVRLNSDGTFE 449

AR15G-2     467  TPVGIDWEGSAENNP-----KDLKCKVTGVGKDVGLIGAFVKCLIIFWDQANRKWFNKPQPETQKIAIKKI 530
C. stercorarium 450 IPGNLEIMSGQPDTWTGTYTGNPNLHVSVYGTDLGAAGSLANALLYYAKTS------GDDEARNLAKEL 513

AR15G-2     531  DIMMTRVRDDKGIATEIERGDVAREMQVMPBKGTKKIMPGKEITEKSKIYETRPDVG-EPLPPIKGP 599
C. stercorarium 514 DRMWNLVRDDKGLISAPETREDYVRFEQEVVMQGWSGTMPCDRIEPGVTFLDTRISKVLNDPYRLQ 583

AR15G-2     600  YGP-KNPARKYRIHRTWQQIAHTLAYGVSMFYEEEVK*  636
C. stercorarium 584 QAYNEGKARVFNHRFMAQCDEIAIANGLVSIL        615
```

THERMOSTABLE CELLOBIOHYDROLASE

TECHNICAL FIELD

The present invention relates to a thermostable cellobiohydrolase, a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Priority is claimed on Japanese Unpublished Patent Application No. 2014-252068, filed Dec. 12, 2014, the content of which is incorporated herein by reference.

BACKGROUND ART

Plant biomass or lignocellulose is the most plentiful renewable energy source on earth. From the viewpoints of global environmental conservation and the potential exhaustion of fossil fuels, biorefineries which use plant biomass as a raw material for the production of biofuels such as ethanol or the raw materials for chemical products are attracting much attention. The main component of plant biomass dry weight is lignocellulose, which is composed of polysaccharides such as cellulose and hemicellulose, and lignin. For example, polysaccharides can be hydrolyzed by a glycoside hydrolase to form monosaccharides such as glucose and xylose, which can then be used as biofuels or the raw materials for chemical products.

Lignocellulose is recalcitrant due to its highly complex structure, and is difficult to degrade or hydrolyze with a single glycoside hydrolase. The complete hydrolysis of lignocellulose generally requires three types of enzymes, namely an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21), and it is thought that the addition of a further plurality of enzymes including the hemicellulase xylanase (endo-1,4-β-xylanase, EC 3.2.1.8) and other plant cell wall-degrading enzymes is also necessary.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 80° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

When cellulose is hydrolyzed by a cellobiohydrolase, the disaccharide cellobiose is the main product. Cellobiohydrolases include some types which initiate hydrolysis from the reducing ends of cellulose (such as cellobiohydrolases belonging to the GH7 and GH48 families and the like), and some types which initiate hydrolysis from the non-reducing ends (such as cellobiohydrolases belonging to the GH5, GH6 and GH9 families and the like), and it is known that if the two types are used in combination, then the cellulose degradation activity is superior to that when either type is used alone (for example, see Non-Patent Document 1). Among cellobiohydrolases which initiate hydrolysis from the non-reducing ends of cellulose, a cellobiohydrolase of the GH6 family having an optimum temperature exceeding 75° C. has been reported (for example, see Patent Document 1).

However, in the case of cellobiohydrolases which initiate hydrolysis from the reducing ends, few enzymes of high thermal stability are known, and in the case of cellobiohydrolases belonging to the GH7 family, cellobiohydrolases have been isolated from the thermophilic filamentous fungi *Chaetomium thermophilum* (for example, see Non-Patent Document 2) and *Thermoascus aurantiacus* (for example, see Non-Patent Document 3) with optimum temperatures of 75° C. and 65° C. respectively. Further, in terms of cellobiohydrolases belonging to the GH48 family, Cel48A has been isolated from the thermophilic actinomycete *Thermobifida fusca* (for example, see Non-Patent Document 4), and has an optimum temperature of about 60° C.

PRIOR ART LITERATURE

Patent Documents

Patent Document 1: International Patent Publication No. 2014/157492

Non-Patent Documents

Non-Patent Document 1: Boisset et al., Applied and Environmental Microbiology, 2000, vol. 66, pp. 1444 to 1452.
Non-Patent Document 2: Ganju et al., Biochimica et Biophysica Acta, 1989, vol. 993, pp. 266 to 274.
Non-Patent Document 3: Hong et al., Applied Microbiology and Biotechnology, 2003, vol. 63, pp. 42 to 50.
Non-Patent Document 4: Irwin et al., European Journal of Biochemistry, 2000, vol. 267, pp. 4988 to 4997.

SUMMARY OF THE INVENTION

Problems to be Solved by the Invention

The present invention has an object of providing a novel thermostable cellobiohydrolase belonging to the GH48 family, which exhibits cellobiohydrolase activity at least at 75° C., and at 85° C. in the presence of calcium ions, a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Means for Solving the Problem

In order to achieve the above object, the inventors of the present invention extracted DNA directly from the high-temperature soils of hot springs, and by carrying out large-scale metagenomic sequencing of the microbial flora that was difficult to culture, they succeeded in obtaining a thermostable cellobiohydrolase having a novel amino acid sequence, thus enabling them to complete the present invention.

In other words, a thermostable cellobiohydrolase, a polynucleotide, an expression vector, a transformant, a method for producing a thermostable cellobiohydrolase, a cellulase mixture, and a method for producing a cellulose degradation product according to the present invention have the aspects [1] to [12] described below.

[1] A thermostable cellobiohydrolase, having a cellobiohydrolase catalytic domain including:

(A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of phosphoric acid swollen Avicel at least under conditions of 75° C. and pH 5, or (C) a polypeptide including an amino acid sequence having 60% or greater sequence identity with the amino acid sequence represented by SEQ ID NO: 1 or 2, and having hydrolysis activity against a substrate of phosphoric acid swollen Avicel at least under conditions of 75° C. and pH 5.

[2] The thermostable cellobiohydrolase according to [1] which, in the presence of calcium ions, exhibits hydrolysis activity against a substrate of phosphoric acid swollen Avicel at least under conditions of 85° C. and pH 5.

[3] The thermostable cellobiohydrolase according to [1] or [2], which also exhibits hydrolysis activity against a substrate of Avicel.

[4] A polynucleotide, having a region encoding a cellobiohydrolase catalytic domain, the region including:

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of phosphoric acid swollen Avicel at least under conditions of 75° C. and pH 5, (c) a nucleotide sequence encoding a polypeptide which includes an amino acid sequence having 60% or greater sequence identity with the amino acid sequence represented by SEQ ID NO: 1 or 2, and has hydrolysis activity against a substrate of phosphoric acid swollen Avicel at least under conditions of 75° C. and pH 5, (d) a nucleotide sequence having 60% or greater sequence identity with a nucleotide sequence represented by SEQ ID NO: 3 or 4, and encoding a polypeptide that has hydrolysis activity against a substrate of phosphoric acid swollen Avicel at least under conditions of 75° C. and pH 5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of phosphoric acid swollen Avicel at least under conditions of 75° C. and pH 5.

[5] The polynucleotide according to [4], wherein the polypeptide also exhibits, in the presence of calcium ions, hydrolysis activity against a substrate of phosphoric acid swollen Avicel at least under conditions of 85° C. and pH 5.

[6] The polynucleotide according to [4] or [5], wherein the polypeptide also exhibits hydrolysis activity against a substrate of Avicel.

[7] An expression vector incorporating the polynucleotide according to any one of [4] to [6], the expression vector being capable of expressing a polypeptide having cellobiohydrolase activity in a host cell.

[8] A transformant into which the expression vector according to [7] has been introduced.

[9] The transformant according to [8], which is a eukaryote.

[10] A method for producing a thermostable cellobiohydrolase, the method including generating the thermostable cellobiohydrolase in the transformant according to [8] or [9].

[11] A glycoside hydrolase mixture, including the thermostable cellobiohydrolase according to any one of [1] to [3], a thermostable cellobiohydrolase encoded by the polynucleotide according to any one of [4] to [6], or a thermostable cellobiohydrolase produced by the method for producing a thermostable cellobiohydrolase according to [10], and at least one other glycoside hydrolase.

[12] A method for producing a cellulose degradation product, the method including generating the cellulose degradation product by bringing a material containing cellulose into contact with the thermostable cellobiohydrolase according to any one of [1] to [3], a thermostable cellobiohydrolase encoded by the polynucleotide according to any one of [4] to [6], the transformant according to [8] or [9], a thermostable cellobiohydrolase produced by the method for producing a thermostable cellobiohydrolase according to [10], or the glycoside hydrolase mixture according to [11].

Effects of the Invention

The thermostable cellobiohydrolase according to the present invention has cellobiohydrolase activity at least at 75° C. and pH 5. For this reason, the thermostable cellobiohydrolase is suitable for hydrolysis processes of materials containing cellulose under high-temperature conditions.

Furthermore, the polynucleotide according to the present invention, an expression vector incorporating the polynucleotide, and a transformant into which the expression vector has been introduced can be used favorably in the production of the thermostable cellobiohydrolase according to the present invention.

BRIEF DESCRIPTION OF THE DRAWINGS

FIG. 1 is an alignment diagram of the amino acid sequence (SEQ ID NO: 1) of an open reading frame AR15G-2 and the amino acid sequence (SEQ ID NO: 9) of an exoglucanase 2 of the Firmicutes bacterium *Clostridium stercorarium* subsp. *stercorarium* DSM 8532.

DETAILED DESCRIPTION OF THE INVENTION

[Thermostable Cellobiohydrolase]

Figure 2:
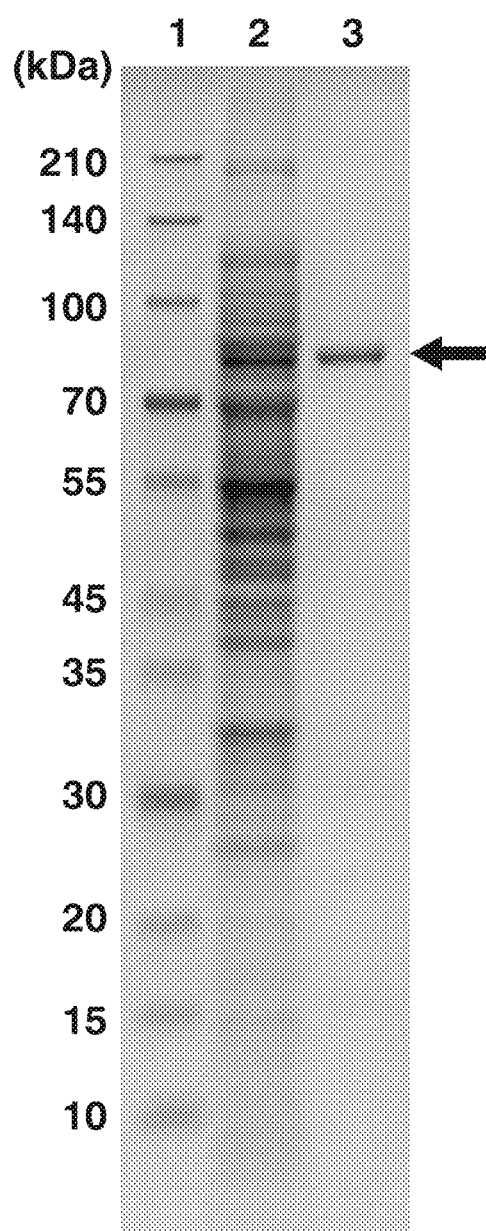
FIG. 2 is a diagram showing the SDS-PAGE analysis results of the AR15G-2-16 protein obtained by expressing the AR15G-2-16 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable cellobiohydrolases.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from high-temperature hot spring soils (for example, hot spring water of 58 to 78° C. containing soil, mud, biomat and biofilm and the like) collected from 5 locations in Japan, and conducted shotgun sequencing and annotation of the metagenomic DNA, thus obtaining open reading frames (ORFs) having amino acid sequences similar to those of known cellobiohydrolases. Primers were then designed based on the nucleotide sequence information of the obtained ORFs, and gene candidates were cloned from the metagenomic DNA of the high-temperature hot spring soils by the PCR method. The PCR-cloned DNAs were incorporated into E. coli, and proteins encoded by these nucleotide sequences were expressed and subjected to functional screening by phosphoric acid swollen Avicel (hereafter often abbreviated as PSA) degradation activity assay. Finally, a thermostable cellobiohydrolase (hereafter also referred to as "AR15G-2-16") having PSA degradation activity was obtained from these ORFs.

The amino acid sequence of AR15G-2-16 is represented by SEQ ID NO: 2, and the nucleotide sequence encoding the amino acid sequence of AR15G-2-16 is represented by SEQ ID NO: 4.

As shown below in Example 1 described below, AR15G-2-16 exhibits a high level of hydrolysis activity against PSA, and also exhibits hydrolysis activity against crystalline cellulose Avicel, but exhibits almost no hydrolysis activity against other substrates. This substrate specificity suggests that AR15G-2-16 is a glycoside hydrolase having cellobiohydrolase activity.

In the present description, the expression "cellobiohydrolase activity" means activity which produces cellobiose when a compound containing β-glycosidic linkages is used as a substrate, and the substrate is subjected to hydrolysis. Examples of the "compound containing β-glycosidic linkages" include glucans having β-glycosidic linkages and oligosaccharides having β-glycosidic linkages.

Further, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has cellobiohydrolase activity" means that the enzyme acts at least against substrates composed of compounds containing β-glycosidic linkages, and generates a significant difference in the amount of reducing ends or the color development reaction of the hydrolyzed substrate compared with a negative control.

Further, in another aspect, the expression "has cellobiohydrolase activity" means that the enzyme acts at least against a substrate of PSA, and preferably acts at least against substrates of PSA and Avicel, and generates a significant difference in the amount of reducing ends or the color development reaction of the hydrolyzed substrate compared with a negative control.

When the amino acid sequence of AR15G-2-16 was searched against a database of known amino acid sequences, the amino acid sequence that showed the highest sequence identity was that of an exoglucanase 2 (SEQ ID NO: 9) belonging to the GH family 48 of Firmicutes bacterium *Clostridium stercorarium* subsp. *stercorarium* DSM 8532, but the sequence identity (homology) in the GH48 catalytic domain was a mere 44%. Based on the substrate specificity and the sequence identity of the amino acid sequence with that of known cellobiohydrolases, it was clear that AR15G-2-16 was a novel cellobiohydrolase belonging to the GH48 family.

AR15G-2-16 has cellobiohydrolase activity at least under conditions of 75° C. and pH 5. Actually, as shown below in Example 1, AR15G-2-16 exhibits cellobiohydrolase activity within a broad temperature range from 50 to 80° C., and across a broad pH range from 4 to 8. More specifically, the cellobiohydrolase activity of AR15G-2-16 increases with increasing temperature within a range from 50 to 75° C., but then tends to decrease rapidly above 75° C.

Further, in the presence of divalent metal ions, AR15G-2-16 exhibits high cellobiohydrolase activity at even higher temperatures than those observed in the absence of such metal ions. Actually, as shown below in Example 1, in the presence of calcium ions, AR15G-2-16 exhibits cellobiohydrolase activity within a broad temperature range from 65 to 90° C., and across a broad pH range from 4 to 8.

Generally, in a protein having some form of bioactivity, one or more amino acids can be deleted, substituted, or added, without impairing the bioactivity. In other words, in AR15G-2-16, one or more amino acids can be deleted, substituted, or added without impairing the cellobiohydrolase activity.

Hence, the thermostable cellobiohydrolase according to the present invention is a thermostable cellobiohydrolase having a cellobiohydrolase catalytic domain including any of the following (A) to (C):

(A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of PSA at least under conditions of 75° C. and pH 5, or (C) a polypeptide including an amino acid sequence having 60% or greater sequence identity with the amino acid sequence represented by SEQ ID NO: 1 or 2, and having hydrolysis activity against a substrate of PSA at least under conditions of 75° C. and pH 5.

The amino acid sequence represented by SEQ ID NO: 1 is the amino acid sequence encoded by the open reading frame AR15G-2 (SEQ ID NO: 3) belonging to GH family 48, which was isolated from a hot spring soil sample using the method described below in Example 1, and which, based on database analysis, was predicted as being a cellobiohydrolase candidate sequence.

In the above polypeptide of (B), the number of amino acids deleted, substituted, or added in the amino acid sequence represented by SEQ ID NO: 1 or 2 is preferably 1 to 20, more preferably 1 to 10, and still more preferably 1 to 5.

In the above polypeptide of (C), the sequence identity with the amino acid sequence represented by SEQ ID NO: 1 or 2 is not specifically limited as long as it is 60% or greater but less than 100%, but the sequence identity is preferably 70% or greater but less than 100%, more preferably 80% or greater but less than 100%, still more preferably 85% or greater but less than 100%, still more preferably 90% or greater but less than 100%, and most preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B) and (C) may be artificially designed, or may be homologs of AR15G-2-16 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1 or 2, by using a gene recombination technique to introduce amino acid mutation(s).

Each of the polypeptides of (A) to (C) has cellobiohydrolase activity at least under conditions of 75° C. and pH 5. As a result, a thermostable cellobiohydrolase can be obtained by having any of the polypeptides of (A) to (C) as the cellobiohydrolase catalytic domain.

The thermostable cellobiohydrolase according to the present invention uses PSA as a substrate. The thermostable cellobiohydrolase may also use other β-glucans or oligosaccharides besides PSA as a substrate. Examples of these other β-glucans or oligosaccharides include crystalline celluloses such as Avicel, bacterial microcrystalline cellulose (hereafter sometimes abbreviated as BMCC) and filter paper; carboxymethyl cellulose (CMC); glucans composed of β-1,4 linkages; oligosaccharides composed of β-1,4 linkages such as cellobiose; xylan; p-nitrophenyl-β-D-galactopyranoside (hereafter sometimes abbreviated as PNPGAL); p-nitrophenyl-β-D-xylopyranoside (hereafter often abbreviated as PNPX); glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose.

The thermostable cellobiohydrolase according to the present invention preferably acts against Avicel substrates in addition to PSA.

The thermostable cellobiohydrolase according to the present invention exhibits hydrolysis activity (cellobiohydrolase activity) against a PSA substrate, at least under conditions of pH 5, preferably within a temperature range from 70 to 80° C., more preferably within a temperature range from 60 to 80° C., and still more preferably within a temperature range from 50 to 80° C. The optimum temperature of the thermostable cellobiohydrolase according to the present invention is preferably within a range from 70 to 90° C., and more preferably within a range from 75 to 85° C.

The term "thermostable" used in relation to the thermostable cellobiohydrolase according to the present invention means the cellobiohydrolase has cellobiohydrolase activity within a temperature range from 50 to 80° C.

The optimum pH of the thermostable cellobiohydrolase according to the present invention is within a range from pH 4.5 to 5.5. The thermostable cellobiohydrolase according to the present invention preferably exhibits cellobiohydrolase activity at least within a range from pH 4.5 to 7.0, and more preferably exhibits cellobiohydrolase activity at least within a range from pH 4.0 to 8.0.

The thermostable cellobiohydrolase according to the present invention may also have other cellulose hydrolysis activity besides the cellobiohydrolase activity. Examples of this other cellulose hydrolysis activity include xylanase activity, β-galactosidase activity, endoglucanase activity, xylosidase activity or β-glucosidase activity.

The thermostable cellobiohydrolase according to the present invention may be an enzyme composed solely of the cellobiohydrolase catalytic domain including any of the aforementioned polypeptides of (A) to (C), or may be an enzyme that also includes other domains. Examples of these other domains include other domains of conventionally known cellobiohydrolases besides the cellobiohydrolase catalytic domain. For example, the thermostable cellobiohydrolase according to the present invention also includes enzymes obtained by substituting the cellobiohydrolase catalytic domain in a publicly known cellobiohydrolase with any of the aforementioned polypeptides of (A) to (C).

When the thermostable cellobiohydrolase according to the present invention includes one or more other domains besides the cellobiohydrolase catalytic domain, the thermostable cellobiohydrolase preferably includes a cellulose-binding module. The cellulose-binding module may be positioned upstream (on the N-terminal side) or downstream (on the C-terminal side) of the cellobiohydrolase catalytic domain. Further, the cellulose-binding module and the cellobiohydrolase catalytic domain may be either bonded directly or bonded via a linker region of appropriate length. In the thermostable cellobiohydrolase according to the present invention, a cellulose-binding module preferably exists either upstream or downstream from the cellobiohydrolase catalytic domain with a linker region positioned therebetween, and a thermostable cellobiohydrolase in which a cellulose-binding module exists upstream of the cellobiohydrolase catalytic domain with a linker region positioned therebetween is particularly preferred.

The cellulose binding module included in the thermostable cellobiohydrolase according to the present invention is a region having the ability to bind cellulose, such as the ability to bind PSA or crystalline Avicel, and there are no particular limitations on the amino acid sequence of the module. Examples of the aforementioned cellulose-binding module include the types of cellulose-binding modules present in known proteins, and appropriately modified versions thereof. Further, in those cases where the thermostable cellobiohydrolase according to the present invention includes both the cellobiohydrolase catalytic domain and a cellulose-binding module, it is preferable that these are bonded via a linker sequence. There are no particular limitations on the amino acid sequence or the length and the like of the linker sequence.

The thermostable cellobiohydrolase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence.

Furthermore, the thermostable cellobiohydrolase according to the present invention may also have various types of tags added, for example at the N-terminal or the C-terminal, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the thermostable cellobiohydrolase according to the present invention contains a cellobiohydrolase catalytic domain including any of the aforementioned polypeptides of (A) to (C); and also contains, according to need, at least one moiety selected from the group consisting of a cellulose-binding module positioned either upstream (on the N-terminal side) or downstream (on the C-terminal side) of the cellobiohydrolase catalytic domain, a linker region, a signal peptide added to either the N-terminal or the C-terminal of the thermostable cellobiohydrolase, and a tag added to either the N-terminal or the C-terminal of the thermostable cellobiohydrolase.

[Polynucleotide Encoding Thermostable Cellobiohydrolase]

The polynucleotide according to the present invention encodes the thermostable cellobiohydrolase according to the present invention. By introducing an expression vector incorporating the polynucleotide into a host, the thermostable cellobiohydrolase can be produced by using the expression system of the host.

Specifically, the polynucleotide according to the present invention is a polynucleotide having a region encoding a cellobiohydrolase catalytic domain, the region including any of the following nucleotide sequences (a) to (e):

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of PSA at least under conditions of 75° C. and pH 5, (c) a nucleotide sequence encoding a polypeptide which includes an amino acid sequence having 60% or greater sequence identity with the amino acid sequence represented by SEQ ID NO: 1 or 2, and has hydrolysis activity against a substrate of PSA at least under conditions of 75° C. and pH 5, (d) a nucleotide sequence having 60% or greater sequence identity with a nucleotide sequence represented by SEQ ID NO: 3 or 4, and encoding a polypeptide that has hydrolysis activity against a substrate of PSA at least under conditions of 75° C. and pH 5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of PSA at least under conditions of 75° C. and pH 5.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 3, the nucleotide sequence represented by SEQ ID NO: 4, or a nucleotide sequence obtained by modifying the nucleotide sequence represented by SEQ ID NO: 3 or 4 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 3 or 4 may be chemically synthesized based on the nucleotide sequence information, or may be obtained from the natural world using gene recombination techniques as either a full length gene that encodes AR15G-2-16 (hereafter sometimes referred to as the "AR15G-2-16 gene" or the "gene clone AR15G-2-16") or a partial region thereof including the cellobiohydrolase catalytic domain. The full length of the AR15G-2-16 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 3 or 4. The cDNA synthesized by a reverse transcription reaction using mRNA recovered from the sample as a template may also be used as a template. The sample from which the nucleic acid used as a template is recovered is preferably a sample collected from a high-temperature environment such as a hot spring soil.

In the aforementioned nucleotide sequence of (d), the sequence identity with the nucleotide sequence represented by SEQ ID NO: 3 or 4 is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b), (c) or (d) can be artificially synthesized by deleting, substituting, or adding one or a plurality of nucleotides in a polynucleotide including the nucleotide sequence represented by SEQ ID NO: 3 or 4. Further, the nucleotide sequence of (b), (c) or (d) may also be a full length sequence of a homologous gene of the AR15G-2-16 gene or a partial sequence thereof. The homologous gene of the AR15G-2-16 gene can be obtained by a gene recombination technique used in obtaining homologous genes of a gene for which the nucleotide sequence is already known.

The polynucleotide according to the present invention may have only the region encoding the cellobiohydrolase catalytic domain, or may also have, in addition to this region, one or more other regions encoding a cellulose-binding module, a linker sequence, various types of signal peptides, or various types of tags or the like.

In other words, one aspect of the polynucleotide according to the present invention contains a region encoding a β-glucosidase catalytic domain, the region including one of the aforementioned nucleotide sequences of (a) to (e), and also contains, according to need, a region encoding at least one moiety selected from the group consisting of a cellulose-binding module, a linker region, a signal peptide and a tag.

[Expression Vector]

The expression vector according to the present invention incorporates the aforementioned polynucleotide according to the present invention, and is capable of expressing, in a host cell, a polypeptide having cellobiohydrolase activity at least under conditions of 75° C. and pH 5. In other words, the expression vector of the present invention is an expression vector into which the polynucleotide according to the present invention has been incorporated in a state capable of expressing the thermostable cellobiohydrolase according to the present invention. More specifically, an expression cassette composed, in order from the upstream side, of DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques, or a commercially available expression vector preparation kit may be used.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable cellobiohydrolase according to the present invention can be expressed. Conventionally known cellobiohydrolases tend to have a narrow range of expression hosts, meaning heterologous expression is often difficult. However, the thermostable cellobiohydrolase according to the present invention can be expressed in a wide range of expression hosts, including *E. coli*, yeasts, filamentous fungi and higher plant chloroplasts. Accordingly, the host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced. By culturing a transformant of *E. coli*, the thermostable cellobiohydrolase according to the present invention can be generated more easily and in large amounts. On the other hand, because proteins are glycosylated in eukaryotic cells, by using a transformant of a eukaryotic cell, a thermostable cellobiohydrolase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Cellobiohydrolase]

The method for producing a thermostable cellobiohydrolase according to the present invention is a method for generating a thermostable cellobiohydrolase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable cellobiohydrolase according to the present invention can be expressed constitutively within the transformant. On the other hand, in the case of a transformant produced using a so-called expression inducible promoter to induce the expression by means of a specific compound or temperature condition or the like, the thermostable cellobiohydrolase according to the present invention can be expressed in the transformant by conducting an induction treatment suitable for the respective expression-inducing condition.

The thermostable cellobiohydrolase generated by the transformant may be used in a state where it is retained inside the transformant, or may be extracted from the transformant and purified.

The method used for extracting and purifying the thermostable cellobiohydrolase from the transformant is not particularly limited, as long as the method does not impair the activity of the thermostable cellobiohydrolase, and extraction can be carried out by methods commonly used for extracting polypeptides from cells or biological tissue. Examples of the method include a method in which the transformant is immersed in an appropriate extraction buffer to extract the thermostable cellobiohydrolase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable cellobiohydrolase in the liquid extract can be purified by known purification methods such as a salting-out method, ultrafiltration method, or chromatography method.

If the thermostable cellobiohydrolase according to the present invention is expressed in the transformant in a state having a secretory signal peptide, then a solution containing the thermostable cellobiohydrolase can be readily obtained by culturing the transformant and then collecting the culture liquid supernatant obtained by removal of the transformant from the obtained culture. Further, if the thermostable cellobiohydrolase according to the present invention has a tag such as an His tag, then the thermostable cellobiohydrolase in the liquid extract or in the culture supernatant can be easily purified by an affinity chromatography method using the tag.

In other words, the method for producing a thermostable cellobiohydrolase according to the present invention includes generating the thermostable cellobiohydrolase within the transformant according to the present invention, and also includes, according to need, extracting the thermostable cellobiohydrolase from the transformant and purifying the thermostable cellobiohydrolase.

[Glycoside Hydrolase Mixture]

The glycoside hydrolase mixture according to the present invention includes the aforementioned thermostable cellobiohydrolase according to the present invention or a thermostable cellobiohydrolase produced by the method for producing a thermostable cellobiohydrolase according to the present invention, and at least one other glycoside hydrolase. The thermostable cellobiohydrolase produced by the aforementioned method for producing a thermostable cellobiohydrolase according to the present invention may be in a state where it is incorporated inside the transformant, or may be extracted from the transformant and purified. By using the thermostable cellobiohydrolase according to the present invention as a mixture with one or more other glycoside hydrolases in a cellulose hydrolysis reaction, materials composed of lignocellulose containing persistent cellulose can be degraded more efficiently.

There are no particular limitations on the other glycoside hydrolase besides the aforementioned thermostable cellobiohydrolase included in the glycoside hydrolase mixture, as long as it exhibits cellulose hydrolysis activity. Examples of the other glycoside hydrolase besides the aforementioned thermostable cellobiohydrolase included in the glycoside hydrolase mixture include hemicellulases such as xylanases and β-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the aforementioned thermostable cellobiohydrolase, and is more preferably a mixture containing both a hemicellulase and an endoglucanase in addition to the aforementioned thermostable cellobiohydrolase. Among the various possibilities, the glycoside hydrolase mixture according to the present invention is preferably a mixture containing at least one glycoside hydrolase selected from the group consisting of xylanases, β-xylosidases and endoglucanases in addition to the aforementioned thermostable cellobiohydrolase, and is more preferably a mixture containing all of a xylanase, a β-xylosidase and an endoglucanase in addition to the thermostable cellobiohydrolase.

The other glycoside hydrolase included in the glycoside hydrolase mixture is preferably a thermostable glycoside hydrolase having glycoside hydrolase activity at least at 75° C., and is more preferably a thermostable glycoside hydrolase having glycoside hydrolase activity at 70 to 90° C. By ensuring that all of the enzymes contained in the glycoside hydrolase mixture are thermostable (that is, have an optimum temperature for the enzymatic activity or a thermal denaturation temperature (melting temperature) for the enzyme protein of 70° C. or higher), the cellulose hydrolysis reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing cellulose, such as a material composed of lignocellulose containing cellulose, it becomes possible to conduct a hydrolysis reaction of the above material in a high-temperature environment in which the hydrolysis temperature is from 70 to 90° C. (namely, a high-temperature hydrolysis). With this high-temperature hydrolysis, the amount of enzymes and the time required for the hydrolysis can be reduced markedly, and the hydrolysis costs can be cut dramatically.

[Method for Producing Cellulose Degradation Product]

The method for producing a cellulose degradation product according to the present invention is a method for obtaining a cellulose degradation product by hydrolyzing a material containing cellulose with the thermostable cellobiohydrolase according to the present invention. More specifically, the method of the present invention is a method of producing a cellulose material degradation product (for example, a degradation product containing cellobiose, glucose or the like) by bringing a material containing cellulose into contact with the thermostable cellobiohydrolase according to the present invention, the transformant according to the present invention, a thermostable cellobiohydrolase produced using the method for producing a thermostable cellobiohydrolase according to the present invention, or the glycoside hydrolase mixture according to the present invention.

There are no particular limitations on the material containing cellulose, provided the material contains cellulose. Specific examples of the material include cellulosic biomass such as weeds and agricultural waste materials, or used paper or the like. The material containing cellulose is preferably subjected to a mechanical treatment such as crushing or shredding, a chemical treatment with acid or alkali or the like, or a treatment such as immersion or dissolution in an appropriate buffer, prior to being brought into contact with the thermostable cellobiohydrolase according to the present invention.

The reaction conditions for the hydrolysis reaction of the above material by the thermostable cellobiohydrolase according to the present invention may be any conditions under which the thermostable cellobiohydrolase exhibits cellobiohydrolase activity. For example, in the absence of divalent metal ions, the reaction is preferably conducted at a temperature of 60 to 80° C. and a pH of 4.5 to 8.0, and is more preferably conducted at a temperature of 70 to 80° C. and a pH of 4.5 to 7.0. Further, in the presence of divalent metal ions, the reaction is preferably conducted at a temperature of 65 to 90° C. and a pH of 4.5 to 8.0, and is more preferably conducted at a temperature of 75 to 90° C. and a pH of 4.5 to 7.0. The reaction time for the hydrolysis reaction may be adjusted appropriately with due consideration of the type, the method of pretreatment, and the amount and the like of the cellulose material supplied to the hydrolysis reaction. For example, the hydrolysis reaction may be performed for a reaction time of 10 minutes to 100 hours, but in the case of degradation of a cellulosic biomass, the hydrolysis reaction is typically performed for a reaction time of 1 to 100 hours.

In the hydrolysis reaction of the material containing cellulose, it is also preferable to use at least one other type of glycoside hydrolase in addition to the thermostable cellobiohydrolase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 75° C., and preferably at least at temperatures of 70 to 90° C. Further, one aspect of the aforementioned method for producing a cellulose degradation product uses the thermostable cellobiohydrolase according to the present invention, the transformant according to the present invention, or a thermostable cellobiohydrolase produced by the method for producing a thermostable cellobiohydrolase according to the present invention, whereas another aspect of the method uses the aforementioned glycoside hydrolase mixture.

EXAMPLES

Next, the present invention is described in further detail based on a series of examples, but the present invention is in no way limited by the following examples.

Example 1

Cloning of Novel Thermostable Cellobiohydrolase from Hot Spring Soil

<1> DNA Extraction from Hot Spring Soil and Whole Genome Sequencing (WGS)

With the purpose of searching for genes of novel thermostable cellobiohydrolases (having an optimum temperature of 55° C. or higher) and ultra thermostable cellobiohydrolases (having an optimum temperature of 80° C. or higher), soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, mud and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver. 2, manufactured by Nippon Gene Co., Ltd.). Five μg of the extracted DNA was subjected to shotgun sequencing of the metagenomic DNA using a sequencer GS FLX Titanium 454 manufactured by Roche Diagnostics Ltd.

Metagenomic DNA sequencing of the hot spring soil sample AR15 (hereafter sometimes referred to as the AR15 metagenome) yielded a whole genome sequence (WGS) data set having an average read length of 370 bp, a total read number of 5,419,406, and a total quantity of sequenced genomes of 2,007,725.04 bp.

<2> Assembly and Statistics of Hot Spring Metagenomic Data

The output from the Roche 454 (sff file) was subjected to a second base calling using Pyrobayes (Quinlan et al., Nature Methods, 2008, vol. 5, pp. 179 to 181), and a FASTA format sequence file and quality value file were obtained. Ends were cut from the obtained sequence reads to improve quality, and the reads were assembled using the 454 Life Sciences assembly software Newbler version 2.3. Assembly was performed under settings including "minimum acceptable overlap match (mi)=0.9", "option: -large (for large or complex genomes, speeds up assembly but reduces accuracy)".

The total contig length of all contigs assembled to at least 100 bp totaled 118,600,846 bp, and this data set was used for cellulase gene analysis. Of the total read length of 5,419,406 reads, 4,805,640 reads were assembled into contigs having an average of at least 1,146 bp (a total of 103,508 contigs), of which the maximum contig length was 151,585 bp.

<3> Prediction of Open Reading Frames (ORFs) of Cellobiohydrolase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database (http://www.uniprot.org/), and a proteome local database of these glycoside hydrolase genes was constructed. The annotation software Orphelia (Hoff et al., Nucleic Acids Research, 2009, 37 (Web Server issue: W101 to W105) was used to predict a gene region (=open reading frame) from the contig sequences obtained in the above section <2> (Orphelia option: default (model=Net 700, maxoverlap=60), Metagene option: -m). In order to extract glycoside hydrolase genes from the predicted ORFs, reference was made to the local database using BLASTP (blastall ver. 2.2.18). Furthermore, the option conditions for BLASTP were set such that: "Filter query sequence=false", "Expectation value (E)<1e$^{-20}$" (hereafter, default values were set such that: "Cost to open a gap=-1", "Cost to extended gap=-1", "X dropoff value for gapped alignment=0", "Threshold for extending hits=0", and "Word size=default"), and the hit sequences were collected as glycoside hydrolase genes.

<4> Glycoside Hydrolase (GH) Family Classification of Genes

Functional classification of the sequences collected in section <3> above, including various glycoside hydrolases such as cellulases, endohemicellulases and debranching enzymes, was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each sequence was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence)).

The GH family classification results of the 26 ORFs predicted as cellobiohydrolase candidate sequences (19 full-length ORFs and 7 partial length ORFs) are shown in Table 1. ORFs for which the coverage of the GH catalytic domain sequence was 70% or greater were counted. As shown in Table 1, from the AR15 metagenome, 1 partial length ORF belonging to the GH family 9, 3 full-length ORFs belonging to the GH family 26, and 1 full-length ORF and 1 partial length ORF belonging to the GH family 48 were obtained. Primers were designed for all of these ORFs, and the genes were cloned from the hot spring soil metagenomic DNA by PCR. As a result, the cellobiohydrolase gene AR15G-2-16 (SEQ ID NO: 4) was isolated from the open reading frame AR15G-2 (SEQ ID NO: 3) belonging to the GH family 48 that was predicted as being a cellobiohydrolase candidate sequence.

TABLE 1

| AR15 Metagenome | GH family classification | | | | |
|---|---|---|---|---|---|
| | GH9 | GH26 | GH48 | other | total |
| Full-length ORFs | 0 | 3 | 1 | 15 | 19 |
| Partial length ORFs | 1 | 0 | 1 | 5 | 7 |
| Total number of ORFs | 1 | 3 | 2 | 20 | 26 |

<5> Open Reading Frame AR15G-2

The open reading frame AR15G-2 encoded a polypeptide (SEQ ID NO: 1) composed of 636 amino acid residues and was a full-length sequence (SEQ ID NO: 3), wherein the polypeptide started from a methionine (M) as the amino acid residue at position 1, and the 3' end of the nucleotide sequence encoding the polypeptide ended with a termination codon. Based on the sequence homology of the motif, it was predicted that the 31 amino acid residues from the methionine at position 1 through to the alanine (A) at position 31 encoded by the open reading frame AR15G-2 represented a secretory signal (SignalP 4.1), and the 592 amino acid residues from the tyrosine (Y) at position 39 through to the phenylalanine (F) at position 630 represented the catalytic domain of the glycoside hydrolase family 48. The ORF was a novel sequence for which the amino acid sequence encoded by the ORF exhibited 43% amino acid sequence identity with the full length of the exoglucanase 2 belonging to GH48 family of the Firmicutes bacterium *Clostridium stercorarium* subsp. *stercorarium* DSM 8532 (Genbank registration ID: AGC68874.1) (SEQ ID NO: 9), and 44% amino acid sequence identity with the GH48 catalytic domain. The sequence homology values were calculated using the ClustalW algorithm.

FIG. 1 shows the alignment of the amino acid sequence (SEQ ID NO: 1) of the open reading frame AR15G-2 and the amino acid sequence (SEQ ID NO: 9) of the GH48 catalytic domain of the exoglucanase 2 of the Firmicutes bacterium *Clostridium stercorarium* subsp. *stercorarium* DSM 8532. In FIG. 1, the amino acids shown in white on black are the amino acid residues identical to both amino acid sequences, the amino acids shown on a grey background indicate positions where the amino acid residues in the sequences are similar, and "-" indicates a gap in a sequence.

<6> Gene Cloning

Using a forward primer including a nucleotide sequence represented by SEQ ID NO: 7 (5'-GTATGA-TAAAATTTCAAAAAAGCGTTTTA-3': wherein two nucleotides (GT) were added to the 5'-end of the nucleotide sequence represented by SEQ ID NO: 5, and the 5'-end was phosphorylated), and a reverse primer including a nucleotide sequence represented by SEQ ID NO: 8 (5'-TAGAGCTCT-TATTTCACCTCTTCTCATATAAAC-3': wherein a recognition sequence for the restriction enzyme SacI was added to the 5'-end of the nucleotide sequence represented by SEQ ID NO: 6, the SacI being a sequence used for vector insertion), a PCR product that had been amplified by KOD-Plus-Neo (manufactured by Toyobo Co., Ltd.) was inserted into a pLEAD4 vector (manufactured by Nippon Gene Co., Ltd.), and transformed into an *E. coli* JM109 strain. The nucleotide sequence represented by SEQ ID NO: 5 is homologous (identical) with the partial sequence composed of the nucleotides from positions 1 to 27 of the nucleotide sequence represented by SEQ ID NO: 3. Further, the nucleotide sequence represented by SEQ ID NO: 6 is complementary with the partial sequence composed of the nucleotides from positions 1,887 to 1,911 of the nucleotide sequence represented by SEQ ID NO: 3. Positive clones were selected by colony PCR and cultured in an LB liquid medium containing 50 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

PCR cloning was used to obtain the gene clone AR15G-2-16 from the open reading frame AR15G-2. The nucleotide sequence (SEQ ID NO: 4) of the cellobiohydrolase candidate gene AR15G-2-16 included 1,911 bp in a similar manner to the open reading frame AR15G-2 (SEQ ID NO: 3), but differed from the predicted ORF AR15G-2 at one nucleotide. In other words, the nucleotide at position 872 was a thymine (T) in the open reading frame AR15G-2, but was a cytosine (C) in the cloned AR15G-2-16 gene. This difference in the nucleotides at one position was also reflected in a difference in the amino acids, so that the amino acid sequence of the open reading frame AR15G-2 (SEQ ID NO: 1) and the amino acid sequence of the cellobiohydrolase candidate gene AR15G-2-16 (SEQ ID NO: 2) differed at one amino acid residue. In other words, the amino acid residue at position 291 of the amino acid sequence encoded by the open reading frame AR15G-2 was a leucine (L), whereas the equivalent amino acid residue in the amino acid sequence encoded by the cloned AR15G-2-16 gene was a serine (S).

<7> Expression and Purification of Cellobiohydrolase Protein

The transformed E. coli clone having the AR15G-2-16/pLEAD4 plasmid for which the sequence had been confirmed was inoculated into a Turbo Broth medium (manufactured by Athena Environmental Sciences, Inc.) containing 50 mg/L of ampicillin, and was cultured for about 20 hours to express the target protein. Following culturing, the E. coli was collected by centrifugation, and an amount of 50 mM Tris-HCl buffer (pH 8.0) equivalent to 1/10 of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant E. coli containing the target protein. This gene recombinant E. coli crude extract was filtered through a filter (pore size φ=0.45 μm, manufactured by EMD Millipore Corporation), and the resulting filtrate was used as a gene recombinant E. coli homogeneous supernatant.

The gene recombinant E. coli homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting cellobiohydrolase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with cellobiohydrolase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0).

The fractions exhibiting cellobiohydrolase activity were pooled and then concentrated by using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting cellobiohydrolase activity were pooled, and a buffer exchange to a 50 mM Tris-HCl buffer (pH 8.0) and subsequent concentration were performed, yielding a purified enzyme with a final concentration of about 1 mg/mL.

The gene recombinant E. coli homogenous supernatant and the purified enzyme (purified cellobiohydrolase protein) were checked by SDS-PAGE (SDS-polyacrylamide gel electrophoresis) analysis. The SDS-PAGE of the gene recombinant E. coli homogenous supernatant and the purified enzyme was performed using a Mini-PROTEAN TGX Stain-Free gel (manufactured by Bio-Rad Laboratories, Inc.). The supernatant and the purified enzyme were each mixed with Tris-SDS βME treatment solution (manufactured by Cosmo Bio Co. Ltd.) at 1:1, and following treatment of the thus obtained electrophoresis samples at 100° C. for 10 minutes, 10 μL of the gene recombinant E. coli homogenous supernatant and 2 μg of the purified enzyme respectively were subjected to electrophoresis. Following completion of the electrophoresis, the protein bands were visualized and detected by CBB staining.

FIG. 2 shows the SDS-PAGE analysis results of the gene recombinant E. coli homogenous supernatant prepared from the transformed E. coli into which the AR15G-2-16 gene had been introduced, and the purified enzyme produced from the gene recombinant E. coli homogenous supernatant. The figure shows an electrophoretic pattern in which lane 1 represents a protein mass marker, lane 2 represents the gene recombinant E. coli homogenous supernatant, and lane 3 represents the purified enzyme. The results revealed a strong band in the gene recombinant E. coli homogenous supernatant (lane 2) near the mass of 74.7 kDa expected from the amino acid sequence (SEQ ID NO: 2), and a single band corresponding with this band (indicated by an arrow in the figure) was observed in the purified enzyme (lane 3).

<8> Measurement of Cellobiohydrolase Activity Against PSA Substrate

The cellobiohydrolase activity of the enzyme protein (AR15G-2-16) encoded by the AR15G-2-16 gene against a substrate of PSA was investigated. In the measurements, a solution prepared by diluting the purified enzyme obtained in section <7> above with a 0.05 M Tris-HCl buffer (pH 8.0) to obtain a concentration of 1 mg/mL was used.

PSA was used as the substrate for measuring the cellobiohydrolase activity. The PSA used as the substrate was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or greater was obtained. The PSA used in the experiments described below was all prepared by the above method.

A sample tube with a volume of 1.5 mL was used as the reaction vessel, and the reaction solution was composed of 10 μL of the diluted purified enzyme, 40 μL of purified water, 50 μL of a 200 mM acetate buffer (pH 5), and 100 μL of a 1% by mass PSA solution. In all measurements, a mixed solution prepared by replacing the purified enzyme solution with a 50 mM Tris-HCl buffer (pH 8.0) and then reacting the solution under the same conditions was used as a control. Further, the substrate solution and the mixed solution containing the purified enzyme solution, the purified water and the buffer were held separately at the reaction temperature for five minutes (pre-incubation) before being mixed to initiate the reaction.

During reaction, all of the mixed solutions were adjusted to the prescribed temperature using a Thermomixer (manufactured by Eppendorf AG). Following completion of the 20-minute reaction, 3,5-dinitrosalicylic acid reagent (DNS solution) was added to each mixed solution in a volume equal to that of the solution, and the resulting mixture was heated at 100° C. for 5 minutes, cooled on ice for 5 minutes, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control. The enzymatic activity for producing 1 μmol of reducing sugars per minute was defined as 1 U, and the value obtained by dividing this activity by the amount of protein was defined as the specific activity (U/mg). Each measurement was performed for three independent experiments, and a mean value and a standard error were determined.

<9> Substrate Specificity of AR15G-2-16

The hydrolysis activity of the enzyme protein AR15G-2-16 against various cellulose substrates and hemicellulose substrates was investigated. In the measurements, a solution prepared by diluting the purified enzyme obtained in section <7> above with a 0.05 M Tris-HCl buffer (pH 8.0) to obtain a concentration of 1 mg/mL was used. For the substrates, PSA, Avicel powder, CMC (manufactured by Sigma-Aldrich Co. LLC.), xylan (derived from beech wood, manufactured by Sigma-Aldrich Co. LLC.), lichenan (manufactured by MP Biomedicals, LLC), laminarin (derived from *Laminaria digitata*, manufactured by Sigma-Aldrich Co. LLC.), PNPC (p-nitrophenyl-β-D-cellobioside, manufactured by Sigma-Aldrich Co. LLC.) and PNPG (p-nitrophenyl-β-D-glucopyranoside, manufactured by Sigma-Aldrich Co. LLC.) were used.

Specifically, when PSA, Avicel powder, CMC, xylan, lichenan or laminarin was used as the substrate, with the exception of using a 1% by mass aqueous solution as the substrate solution and performing the reaction at 70° C., reaction was performed in the same manner as that described above in section <8>, the amount of reducing sugars produced by the enzymatic hydrolysis was determined, and the specific activity (U/mg) was calculated. For the xylan measurement, a calibration curve prepared using xylose was used.

When PNPC or PNPG was used as the substrate, with the exception of using a 10 mM aqueous solution as the substrate solution and performing the reaction at 70° C., reaction was first performed in the same manner as that described above in section <8>, and following the 20-minute reaction, an equal volume of a 200 mM aqueous solution of sodium carbonate was added, and the resulting mixture was then centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control. The enzymatic activity for producing 1 μmol of p-nitrophenol per minute was defined as 1 U, and the value obtained by dividing this activity by the mass of protein was defined as the specific activity (U/mg).

Figure 3:
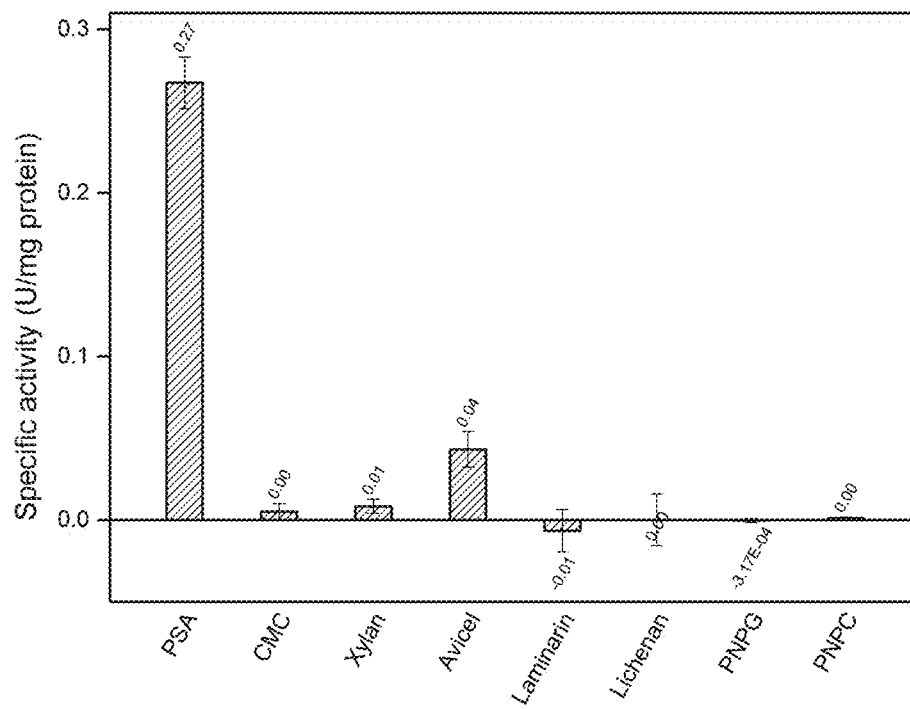
FIG. 3 is a diagram showing the results of measuring the hydrolysis activity against various substrates of the AR15G-2-16 protein obtained by expressing the AR15G-2-16 gene in *E. coli* in Example 1.

The measurement results are shown in FIG. 3. The results revealed that AR15G-2-16 exhibited a high level of hydrolysis activity against PSA, and also exhibited hydrolysis activity against Avicel, but exhibited no hydrolysis activity against the remaining substrates.

<10> Temperature and pH Dependencies of Cellobiohydrolase of AR15G-2-16

The temperature dependency of the PSA hydrolysis activity of AR15G-2-16 was investigated. Specifically, with the exception of setting the reaction temperature to 40, 50, 60, 65, 70, 75, 80, 85, 90 or 95° C., reaction was performed in the same manner as that described above in section <8>, and for each temperature, the amount of reducing sugars produced by the enzymatic hydrolysis was determined and the PSA hydrolysis activity (U/mg) was calculated.

Further, measurements were also performed using reaction solutions in which a 10 mM aqueous solution of $CaCl_2$ was added instead of the 40 μL of purified water, and for each temperature, the amount of reducing sugars produced by the enzymatic hydrolysis was determined and the PSA hydrolysis activity (U/mg) was calculated.

Figure 4:
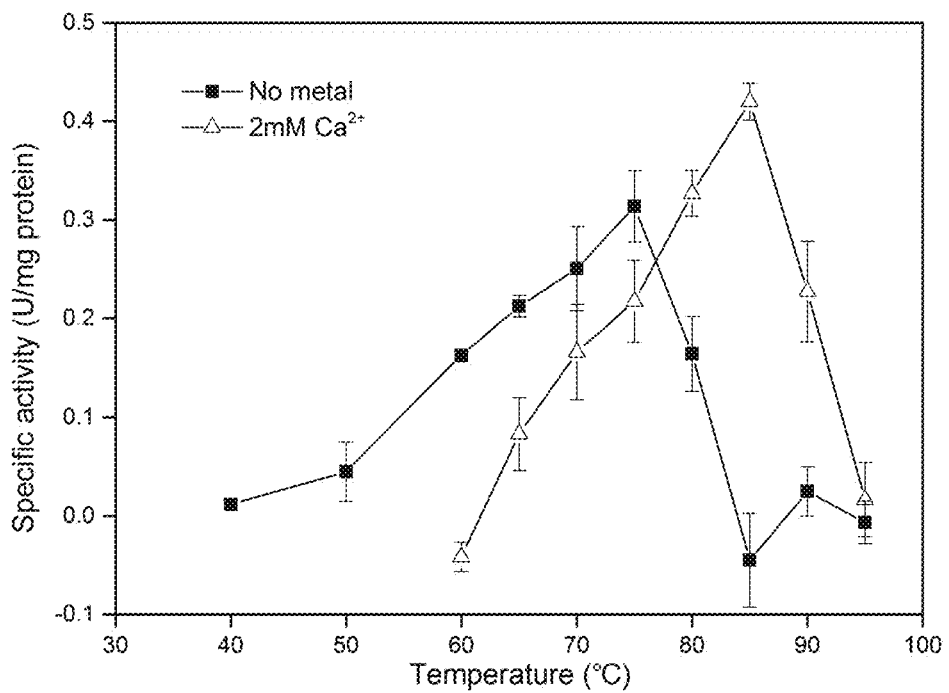
FIG. 4 is a diagram showing the results of measuring the PSA hydrolysis activity (pH 5.0) at various temperatures, either in the presence of calcium ions or in the absence of calcium ions, of the AR15G-2-16 protein obtained by expressing the AR15G-2-16 gene in *E. coli* in Example 1.

The results are shown in FIG. 4. In the absence of calcium ions (labeled as "No metal" in the figure), AR15G-2-16 exhibited PSA hydrolysis activity in a temperature range from 50 to 80° C.

Further, in the presence of calcium ions (labeled as "2 mM $Ca^{2+}$" in the figure), AR15G-2-16 exhibited PSA hydrolysis activity in a temperature range from 65 to 90° C. The optimum temperature ($T_{opt}$) at which the highest activity was observed was 75° C. in the absence of calcium ions and 85° C. in the presence of calcium ions.

The pH dependency of the PSA hydrolysis activity of AR15G-2-16 was also investigated. Specifically, with the exception of performing the reaction at 70° C. using 50 μL of either a 200 mM acetate buffer (pH 4 to 6) or a 200 mM phosphate buffer (pH 6 to 8), reaction was performed in the same manner as that described above in section <8>, and for each pH value, the amount of reducing sugars produced by the enzymatic hydrolysis was determined and the PSA hydrolysis activity (U/mg) was calculated.

Figure 5:
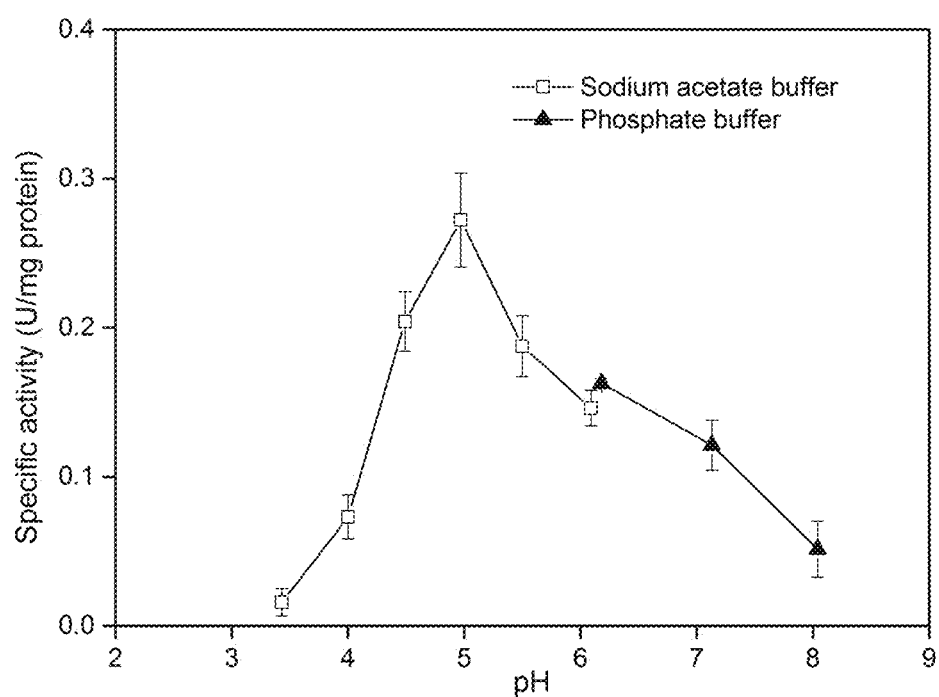
FIG. 5 is a diagram showing the results of measuring the PSA hydrolysis activity (70° C.) at various pH values of the AR15G-2-16 protein obtained by expressing the AR15G-2-16 gene in *E. coli* in Example 1.

The results are shown in FIG. 5. For the pH values, the actual measurement value obtained for the mixed solution containing the substrate, the buffer and the enzyme was plotted. AR15G-2-16 exhibited PSA hydrolysis activity in a pH range from pH 4 to 8.

The optimum pH was 4.97 (actual measurement value for the mixed solution containing the substrate, the buffer and the enzyme).

<11> Thermal Stability Measurement of Cellobiohydrolase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the internal hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm By increasing the temperature of the protein solution at regular intervals in a stepwise manner and measuring the fluorescence intensity, the thermal denaturation temperature (=change point of the fluorescence intensity) can be calculated.

Measurements were performed using a purified enzyme solution prepared by dissolving the purified enzyme AR15G-2-16 obtained in section <7> above in water at a concentration of 1 mg/mL.

Specifically, 2 µL of 100-fold diluted SYPRO Orange (manufactured by Life Technologies Inc.), 1 µL of the purified enzyme solution with a concentration of 1 mg/mL, 5 µL of a 200 mM acetate buffer (pH 5.0) and 12 µL of purified water were added to each well of a 96-well PCR plate (Multiplate 96 Well PCR Plate MLL-9651, manufactured by Bio-Rad Laboratories, Inc.) so that the volume in each well was 20 µL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. The thermal denaturation temperature (melting temperature; Tm value) was defined as the local minimum value of the first derivative ("−d(Fluorescence)/dT" shown on the Y axis of FIG. 6(B)) of the fluorescence intensity curve that is a function of temperature. Data analysis was conducted using the analysis software CFX Manager (manufactured by Bio-Rad Laboratories, Inc.) supplied with the real-time PCR machine.

Figure 6:
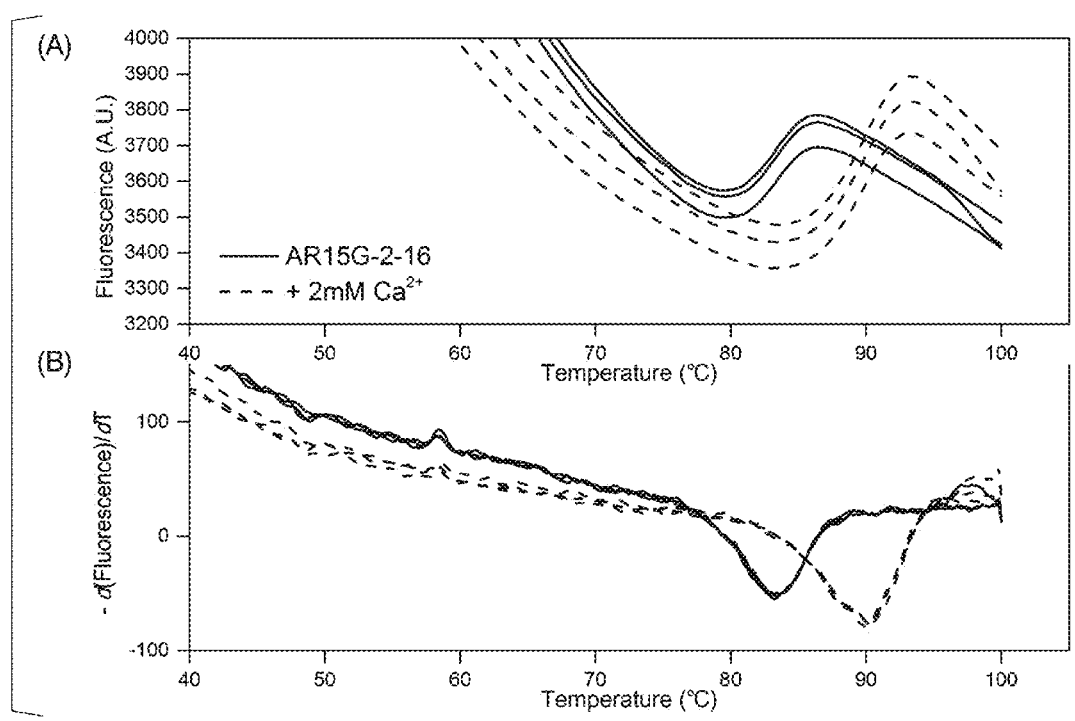
FIG. 6 consists of a diagram (A) and a diagram (B). The diagram (A) shows an actual measurement data of the change in the fluorescence intensity of SYPRO Orange that is generated in association with the thermal denaturation exhibited by the AR15G-2-16 protein obtained by expressing the AR15G-2-16 gene in *E. coli* in Example 1. The diagram (B) shows a first derivative "−d(Fluorescence)/dT" of the fluorescence intensity change curve of the diagram (A).

FIG. 6(A) shows the actual measurement data of the change in the fluorescence intensity of SYPRO Orange measured by the DSF method and caused in association with the thermal denaturation exhibited by the AR15G-2-16 enzyme protein. FIG. 6 (B) shows the first derivative "−d (Fluorescence)/dT" of the fluorescence intensity change curve of FIG. 6(A). Each set of measurements was performed for three independent experiments.

The first derivative of the fluorescence intensity of AR15G-2-16 had a local minimum point near 83.5° C., indicating that thermal denaturation occurs at that temperature. Further, under the conditions including added $CaCl_2$, the local minimum point occurred near 90° C., confirming that the inclusion of calcium ions increased the thermal denaturation temperature by 6.5° C. The average values for the Tm were 83.5±0.2° C. (no $CaCl_2$ addition) and 90.0±0° C. ($CaCl_2$ addition), which were close to the respective optimum temperature values for the enzyme determined on the basis of the PSA hydrolysis activity of 75° C. (no $CaCl_2$ addition) and 85° C. ($CaCl_2$ addition).

The invention claimed is:

1. An isolated recombinant thermostable cellobiohydrolase comprising
   a polypeptide consisting of the amino acid sequence of SEQ ID NO: 1 or 2, and
   at least one moiety selected from the group consisting of a cellulose-binding module, a linker region, a signal peptide and a tag.

2. A glycoside hydrolase mixture, comprising the thermostable cellobiohydrolase according to claim 1 and at least one other glycoside hydrolase.

* * * * *

```
                        SEQUENCE LISTING

<160> NUMBER OF SEQ ID NOS: 9

<210> SEQ ID NO 1
<211> LENGTH: 636
<212> TYPE: PRT
<213> ORGANISM: Unknown
<220> FEATURE:
<223> OTHER INFORMATION: Open reading frame AR15G-2

<400> SEQUENCE: 1

Met Ile Lys Phe Gln Lys Ser Val Leu Thr Trp Leu Cys Ile Ile Leu
1               5                   10                  15

Pro Ile Pro Thr Ala Leu Phe Ser Ala Asp Val Asn Leu Ser Ala Glu
            20                  25                  30

Lys Gln Ser Glu Lys Thr Tyr Lys Tyr Lys Phe Leu Glu Leu Trp Gln
        35                  40                  45

Glu Ile His Asp Pro Asn Asn Gly Tyr Leu Ser Asn Glu Gly Ile Pro
    50                  55                  60

Tyr His Ser Ile Glu Lys Leu Ile Ile Glu Ala His Asp Tyr Gly His
65                  70                  75                  80

His Ser Thr Ser Glu Ala Met Ser Phe Leu Ile Trp Leu Glu Ala Leu
                85                  90                  95

Tyr Ala Tyr Phe Thr Lys Asp Trp Ser Tyr Phe Glu Lys Ser Trp Glu
            100                 105                 110

Val Met Glu Lys Tyr Phe Ile Pro Asp Lys Lys Thr Glu Gln Pro Asn
        115                 120                 125

Met Asp Ala Tyr Asn Phe Asp Lys Pro Ala Ser Tyr Val Pro Glu Tyr
    130                 135                 140

Asp Asp Pro Tyr Lys Tyr Pro Ala Gly Val Ile Tyr Glu Glu Pro Val
```

```
                        145                 150                 155                 160
           Gly Val Asp Pro Leu Asp Asp Val Thr Ala Lys Tyr Gly His Ala Met
                                165                 170                 175
           Tyr Leu Met His Trp Leu Ile Asp Val Asp Asp Trp Tyr Gly Phe Ser
                                180                 185                 190
           Lys Tyr Ser Gly Gly Arg Lys Arg Ala Val Leu Val Asn Leu Phe Gln
                                195                 200                 205
           Arg Gly Pro Asn Glu Ser Thr Trp Glu Thr Ile Pro His Pro Ser Ile
                                210                 215                 220
           Glu Asn Tyr Thr Asn Lys Pro Gln Gly Phe Val Asp Leu Phe Val Gln
           225                 230                 235                 240
           Ser Asn Ala Asn Gln Trp Arg Tyr Thr Ser Ala Pro Asp Ala Glu Ala
                                245                 250                 255
           Arg Val Ala Gln Ala Phe Tyr Trp Ala Glu Glu Phe Ala Arg Gln Gln
                                260                 265                 270
           Lys Trp Gly Lys Ile Ser Asp Tyr Arg Leu Lys Met Tyr Glu Met Gly
                                275                 280                 285
           Asp Trp Leu Arg Tyr Cys Leu Phe Asp Lys Tyr Phe Lys Lys Ile Gly
                                290                 295                 300
           Ala Gly Arg Thr Pro Gly Lys Gly Tyr Asp Ser Cys His Tyr Leu Ile
           305                 310                 315                 320
           Ser Trp Tyr Val Ala Trp Gly Ala Ala Leu Asn Glu Lys Trp Ala Trp
                                325                 330                 335
           Arg Ile Gly Cys Ser Gln Ala His Cys Gly Tyr Gln Asn Pro Leu Gly
                                340                 345                 350
           Ala Tyr Tyr Leu Ser Lys Ile Gly Val Asp Asp Trp Asp Lys Ser Leu
                                355                 360                 365
           Lys Arg Gln Ile Glu Leu Ile Glu Phe Cys Gln Ala Val Asn Gly Ala
                                370                 375                 380
           Ile Gly Gly Gly Val Ile Asn Asp Trp Asp Arg Pro Asn Gly Pro Phe
           385                 390                 395                 400
           Tyr Gly Met His Tyr Ser Gln His Pro Val Tyr Leu Asp Pro Pro Ser
                                405                 410                 415
           Asn Thr Trp Ser Gly Trp Gln Tyr Trp Leu Met Glu Arg Met Phe Gln
                                420                 425                 430
           Tyr Ile Tyr Ala Ser Gly Asp Lys Lys Ala Phe Lys Ile Cys Glu Lys
                                435                 440                 445
           Trp Leu Tyr Glu Trp Ala Leu Lys Glu Met Lys Leu Thr Asp Asn Asp
                                450                 455                 460
           Ile Glu Ile Pro Val Gly Ile Asp Trp Glu Gly Ser Ala Glu Asn Asn
           465                 470                 475                 480
           Pro Lys Asp Leu Lys Cys Lys Val Thr Gly Tyr Gly Lys Asp Val Gly
                                485                 490                 495
           Leu Ile Gly Ala Phe Val Lys Cys Leu Ile Phe Trp Asp Gln Ala Asn
                                500                 505                 510
           Arg Lys Trp Phe Asn Lys Pro Gln Pro Glu Thr Gln Lys Ile Ala Lys
                                515                 520                 525
           Lys Ile Leu Asp Ile Met Trp Thr Arg Tyr Arg Asp Asp Lys Gly Ile
                                530                 535                 540
           Ala Thr Glu Glu Glu Arg Gly Asp Tyr Ala Arg Phe Trp Glu Gln Val
           545                 550                 555                 560
           Val Pro Met Pro Lys Gly Thr Lys Lys Ile Met Pro Trp Gly Lys Glu
                                565                 570                 575
```

```
Ile Thr Glu Lys Ser Lys Phe Tyr Glu Thr Arg Pro Asp Tyr Gly Glu
            580                 585                 590

Pro Leu Pro Pro Lys Gly Pro Tyr Gly Pro Lys Asn Pro Ala Pro Lys
            595                 600                 605

Tyr Arg Tyr His Arg Thr Trp Gln Gln Ile Ala Ile Thr Leu Ala Tyr
    610                 615                 620

Gly Tyr Tyr Ser Met Phe Tyr Glu Glu Val Lys
625                 630                 635

<210> SEQ ID NO 2
<211> LENGTH: 636
<212> TYPE: PRT
<213> ORGANISM: Unknown
<220> FEATURE:
<223> OTHER INFORMATION: AR15G-2-16

<400> SEQUENCE: 2

Met Ile Lys Phe Gln Lys Ser Val Leu Thr Trp Leu Cys Ile Ile Leu
1               5                   10                  15

Pro Ile Pro Thr Ala Leu Phe Ser Ala Asp Val Asn Leu Ser Ala Glu
            20                  25                  30

Lys Gln Ser Glu Lys Thr Tyr Lys Tyr Lys Phe Leu Glu Leu Trp Gln
        35                  40                  45

Glu Ile His Asp Pro Asn Asn Gly Tyr Leu Ser Asn Glu Gly Ile Pro
    50                  55                  60

Tyr His Ser Ile Glu Lys Leu Ile Ile Glu Ala His Asp Tyr Gly His
65                  70                  75                  80

His Ser Thr Ser Glu Ala Met Ser Phe Leu Ile Trp Leu Glu Ala Leu
                85                  90                  95

Tyr Ala Tyr Phe Thr Lys Asp Trp Ser Tyr Phe Glu Lys Ser Trp Glu
            100                 105                 110

Val Met Glu Lys Tyr Phe Ile Pro Asp Lys Lys Thr Glu Gln Pro Asn
        115                 120                 125

Met Asp Ala Tyr Asn Phe Asp Lys Pro Ala Ser Tyr Val Pro Glu Tyr
    130                 135                 140

Asp Asp Pro Tyr Lys Tyr Pro Ala Gly Val Ile Tyr Glu Glu Pro Val
145                 150                 155                 160

Gly Val Asp Pro Leu Asp Asp Val Thr Ala Lys Tyr Gly His Ala Met
                165                 170                 175

Tyr Leu Met His Trp Leu Ile Asp Val Asp Asp Trp Tyr Gly Phe Ser
            180                 185                 190

Lys Tyr Ser Gly Gly Arg Lys Arg Ala Val Leu Val Asn Leu Phe Gln
        195                 200                 205

Arg Gly Pro Asn Glu Ser Thr Trp Glu Thr Ile Pro His Pro Ser Ile
    210                 215                 220

Glu Asn Tyr Thr Asn Lys Pro Gln Gly Phe Val Asp Leu Phe Val Gln
225                 230                 235                 240

Ser Asn Ala Asn Gln Trp Arg Tyr Thr Ser Ala Pro Asp Ala Glu Ala
                245                 250                 255

Arg Val Ala Gln Ala Phe Tyr Trp Ala Glu Glu Phe Ala Arg Gln Gln
            260                 265                 270

Lys Trp Gly Lys Ile Ser Asp Tyr Arg Leu Lys Met Tyr Glu Met Gly
        275                 280                 285

Asp Trp Ser Arg Tyr Cys Leu Phe Asp Lys Tyr Phe Lys Lys Ile Gly
    290                 295                 300
```

Ala Gly Arg Thr Pro Gly Lys Gly Tyr Asp Ser Cys His Tyr Leu Ile
305                 310                 315                 320

Ser Trp Tyr Val Ala Trp Gly Ala Ala Leu Asn Glu Lys Trp Ala Trp
            325                 330                 335

Arg Ile Gly Cys Ser Gln Ala His Cys Gly Tyr Gln Asn Pro Leu Gly
        340                 345                 350

Ala Tyr Tyr Leu Ser Lys Ile Gly Val Asp Asp Trp Asp Lys Ser Leu
    355                 360                 365

Lys Arg Gln Ile Glu Leu Ile Glu Phe Cys Gln Ala Val Asn Gly Ala
370                 375                 380

Ile Gly Gly Val Ile Asn Asp Trp Asp Arg Pro Asn Gly Pro Phe
385                 390                 395                 400

Tyr Gly Met His Tyr Ser Gln His Pro Val Tyr Leu Asp Pro Pro Ser
            405                 410                 415

Asn Thr Trp Ser Gly Trp Gln Tyr Trp Leu Met Glu Arg Met Phe Gln
        420                 425                 430

Tyr Ile Tyr Ala Ser Gly Asp Lys Lys Ala Phe Lys Ile Cys Glu Lys
    435                 440                 445

Trp Leu Tyr Glu Trp Ala Leu Lys Glu Met Lys Leu Thr Asp Asn Asp
    450                 455                 460

Ile Glu Ile Pro Val Gly Ile Asp Trp Glu Gly Ser Ala Glu Asn Asn
465                 470                 475                 480

Pro Lys Asp Leu Lys Cys Lys Val Thr Gly Tyr Gly Lys Asp Val Gly
            485                 490                 495

Leu Ile Gly Ala Phe Val Lys Cys Leu Ile Phe Trp Asp Gln Ala Asn
        500                 505                 510

Arg Lys Trp Phe Asn Lys Pro Gln Pro Glu Thr Gln Lys Ile Ala Lys
    515                 520                 525

Lys Ile Leu Asp Ile Met Trp Thr Arg Tyr Arg Asp Asp Lys Gly Ile
    530                 535                 540

Ala Thr Glu Glu Glu Arg Gly Asp Tyr Ala Arg Phe Trp Glu Gln Val
545                 550                 555                 560

Val Pro Met Pro Lys Gly Thr Lys Lys Ile Met Pro Trp Gly Lys Glu
            565                 570                 575

Ile Thr Glu Lys Ser Lys Phe Tyr Glu Thr Arg Pro Asp Tyr Gly Glu
        580                 585                 590

Pro Leu Pro Pro Lys Gly Pro Tyr Gly Pro Lys Asn Pro Ala Pro Lys
    595                 600                 605

Tyr Arg Tyr His Arg Thr Trp Gln Gln Ile Ala Ile Thr Leu Ala Tyr
    610                 615                 620

Gly Tyr Tyr Ser Met Phe Tyr Glu Glu Glu Val Lys
625                 630                 635

<210> SEQ ID NO 3
<211> LENGTH: 1911
<212> TYPE: DNA
<213> ORGANISM: Unknown
<220> FEATURE:
<223> OTHER INFORMATION: Open reading frame AR15G-2

<400> SEQUENCE: 3
atgataaaat ttcaaaaaag cgttttaacc tggctgtgta taatcttgcc aataccaact      60
gctttattct cagcagatgt gaatctttct gcagaaaaac aaagtgaaaa acatatataaa    120 tataaatttt tagaactgtg gcaagaaatt catgacccca caacggata tttatcaaac     180

```
gaaggaatcc cataccatag tatagaaaaa cttataatag aagctcatga ttatggccat    240
cattccacaa gtgaagcaat gtcatttctt atatggcttg aagcgttata tgcatacttt    300
acaaaagatt ggtcttattt tgaaaaatca tgggaagtga tggaaaaata ttttatacct    360
gacaaaaaga cagaacaacc caatatggat gcttataatt ttgataagcc cgcatcttat    420
gttcctgaat atgatgaccc atacaaatat ccagcaggtg ttatctatga agaaccggta    480
ggagttgatc cacttgatga tgttacagca aaatatggac atgcaatgta tcttatgcat    540
tggcttatag atgtagacga ttggtacggt tttagcaaat attccggtgg aagaaaaaga    600
gccgttttag taaatttatt ccaaagagga ccaaatgaat caacttggga aacaatacca    660
catccaagta tagaaaatta tacaaacaaa cctcaagggt tgttgaccct ttttgttcaa    720
tcgaacgcta accagtggag atacacctct gctccagatg ctgaggcaag ggttgcacag    780 gcatttatt gggctgagga gtttgcgaga caacaaaaat ggggtaaaat ttctgactat    840
agattaaaaa tgtatgaaat gggtgattgg ttgagatatt gtctgtttga caaatacttc    900 aaaaaattg gagctggaag aactcctggg aaagggtatg atagctgtca ttatttaatt    960
tcttggtatg tagcatgggg agcagcatta acgaaaagt gggcttggag aataggttgc   1020
agccaagcac attgcggtta tcaaaatccg cttggagctt attacttatc aaaaattggt   1080
gttgacgact gggacaaatc attaaaaagg caaattgaac ttatagaatt ctgtcaggca   1140
gtaaacggag caataggtgg tggagttatc aatgactggg ataggccaaa tggaccattt   1200
tatggtatgc attattctca acatccagta tatctagacc caccaagcaa tacttggtct   1260
ggttggcagt attggcttat ggaaagaatg tttcaatata tttacgcttc tggagataaa   1320
aaagcattta aaatttgtga gaatggcctt tatgagtggg cattaaaaga gatgaaacta   1380
acagacaatg acatagaaat tcctgtaggg attgactggg aaggttctgc tgaaaataat   1440
ccaaaggatt taaaatgtaa agttactggt tatggaaaag atgttggttt aatcggagct   1500
tttgttaaat gtttaatttt ctgggatcaa gcaaatagaa aatggtttaa caaacctcaa   1560
ccagaaacac aaaaaaattgc aaaaaaaatt ttggatataa tgtggacaag atatagagat   1620
gataaaggta ttgcgacaga agaagaacga ggagattatg caagattctg gaacaagta   1680 gtacctatgc caaaggaac aaaaaaaatc atgccttggg gtaaagagat tactgaaaaa   1740
tcaaaatttt atgaaacaag acctgactat ggtgaaccac ttcccccaaa aggaccatat   1800
ggtccaaaaa atcctgcacc aaagtataga tatcacagaa cttggcaaca aattgctata   1860
actttagctt atggatatta tagtatgttt tatgaagaag aggtgaaata a            1911
```

<210> SEQ ID NO 4
<211> LENGTH: 1911
<212> TYPE: DNA
<213> ORGANISM: Unknown
<220> FEATURE:
<223> OTHER INFORMATION: AR15G-2-16

<400> SEQUENCE: 4

```
atgataaaat ttcaaaaaag cgttttaacc tggctgtgta taatcttgcc aataccaact     60
gctttattct cagcagatgt gaatctttct gcagaaaaca aaagtgaaaa aacatataaa    120
tataaatttt tagaactgtg gcaagaaatt catgaccccca caacggata tttatcaaac    180 gaaggaatcc cataccatag tatagaaaaa cttataatag aagctcatga ttatggccat    240
cattccacaa gtgaagcaat gtcatttctt atatggcttg aagcgttata tgcatacttt    300
```

-continued

| | |
|---|---|
| acaaaagatt ggtcttattt tgaaaaatca tgggaagtga tggaaaaata ttttatacct | 360 |
| gacaaaaaga cagaacaacc caatatggat gcttataatt ttgataagcc cgcatcttat | 420 |
| gttcctgaat atgatgaccc atacaaatat ccagcaggtg ttatctatga agaaccggta | 480 |
| ggagttgatc cacttgatga tgttacagca aaatatggac atgcaatgta tcttatgcat | 540 |
| tggcttatag atgtagacga ttggtacggt tttagcaaat attccggtgg aagaaaaaga | 600 |
| gccgttttag taaatttatt ccaaagagga ccaaatgaat caacttggga aacaatacca | 660 |
| catccaagta tagaaaatta tacaaacaaa cctcaagggt tgttgacct ttttgttcaa | 720 |
| tcgaacgcta accagtggag atacacctct gctccagatg ctgaggcaag ggttgcacag | 780 |
| gcattttatt gggctgagga gtttgcgaga caacaaaaat ggggtaaaat ttctgactat | 840 |
| agattaaaaa tgtatgaaat gggtgattgg tcgagatatt gtctgtttga caaatacttc | 900 |
| aaaaaaattg gagctggaag aactcctggg aaagggtatg atagctgtca ttatttaatt | 960 |
| tcttggtatg tagcatgggg agcagcatta acgaaaagt gggcttggag aataggttgc | 1020 |
| agccaagcac attgcggtta tcaaaatccg cttggagctt attacttatc aaaaattggt | 1080 |
| gttgacgact gggacaaatc attaaaaagg caaattgaac ttatagaatt ctgtcaggca | 1140 |
| gtaaacggag caataggtgg tggagttatc aatgactggg ataggccaaa tggaccattt | 1200 |
| tatggtatgc attattctca acatccagta tatctagacc caccaagcaa tacttggtct | 1260 |
| ggttggcagt attggcttat ggaagaatg tttcaatata tttacgcttc tggagataaa | 1320 |
| aaagcattta aaatttgtga gaaatggctt tatgagtggg cattaaaaga gatgaaacta | 1380 |
| acagacaatg acatagaaat tcctgtaggg attgactggg aaggttctgc tgaaaataat | 1440 |
| ccaaaggatt taaatgtaa agttactggt tatggaaaag atgttggttt aatcggagct | 1500 |
| tttgttaaat gtttaatttt ctgggatcaa gcaaatagaa aatggtttaa caaacctcaa | 1560 |
| ccagaaacac aaaaaattgc aaaaaaaatt ttggatataa tgtggacaag atatagagat | 1620 |
| gataaaggta ttgcgacaga agaagaacga ggagattatg caagattctg ggaacaagta | 1680 |
| gtacctatgc caaaaggaac aaaaaaaatc atgccttggg gtaaagagat tactgaaaaa | 1740 |
| tcaaaatttt atgaaacaag acctgactat ggtgaaccac ttcccccaaa aggaccatat | 1800 |
| ggtccaaaaa atcctgcacc aaagtataga tatcacgaa cttggcaaca aattgctata | 1860 |
| actttagctt atggatatta tagtatgttt tatgaagaag aggtgaaata a | 1911 |

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer.

<400> SEQUENCE: 5
atgataaaat ttcaaaaaag cgtttta                                      27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer.

<400> SEQUENCE: 6
ttatttcacc tcttcttcat aaaac                                        25

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer.

<400> SEQUENCE: 7
gtatgataaa atttcaaaaa agcgtttta                              29

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 8
tagagctctt atttcacctc ttcttcataa aac                         33

<210> SEQ ID NO 9
<211> LENGTH: 914
<212> TYPE: PRT
<213> ORGANISM: Clostridium stercorarium subsp. stercorarium DSM 8532
<220> FEATURE:
<223> OTHER INFORMATION: Exoglucanase 2

<400> SEQUENCE: 9

Met Lys Arg Arg Leu Met Lys Gly Ile Ser Leu Leu Thr Leu Val Phe
1               5                   10                  15

Leu Ile Gly Ile Met Leu Gln Leu Ser Leu Lys Ser Glu Leu Thr Ala
            20                  25                  30

Tyr Ala Ser Ser Asp Asp Pro Tyr Lys Gln Arg Phe Leu Glu Leu Trp
        35                  40                  45

Glu Glu Leu His Asp Pro Ser Asn Gly Tyr Phe Ser Ser His Gly Ile
    50                  55                  60

Pro Tyr His Ala Val Glu Thr Leu Ile Val Ala Pro Asp Tyr Gly
65                  70                  75                  80

His Leu Thr Thr Ser Glu Ala Met Ser Tyr Tyr Leu Trp Leu Glu Ala
                85                  90                  95

Leu Tyr Gly Lys Phe Thr Gly Asp Phe Ser Tyr Phe Met Lys Ala Trp
            100                 105                 110

Glu Thr Ile Glu Lys Tyr Met Ile Pro Thr Glu Gln Asp Gln Pro Asn
        115                 120                 125

Arg Ser Met Ala Gly Tyr Asn Pro Ala Lys Pro Ala Thr Tyr Ala Pro
    130                 135                 140

Glu Trp Glu Glu Pro Ser Met Tyr Pro Ser Gln Leu Asp Phe Ser Ala
145                 150                 155                 160

Pro Val Gly Ile Asp Pro Ile Tyr Asn Glu Leu Val Ser Thr Tyr Gly
                165                 170                 175

Thr Asn Thr Ile Tyr Gly Met His Trp Leu Leu Asp Val Asp Asn Trp
            180                 185                 190

Tyr Gly Phe Gly Arg Arg Ala Asp Arg Ile Ser Ser Pro Ala Tyr Ile
        195                 200                 205

Asn Thr Phe Gln Arg Gly Ser Gln Glu Ser Val Trp Glu Thr Ile Pro
    210                 215                 220

Gln Pro Cys Trp Asp Asp Leu Thr Ile Gly Gly Arg Asn Gly Phe Leu
225                 230                 235                 240

Asp Leu Phe Val Gly Asp Ser Gln Tyr Ser Ala Gln Phe Lys Tyr Thr

```
            245                 250                 255
Asn Ala Pro Asp Ala Asp Ala Arg Ala Ile Gln Ala Thr Tyr Trp Ala
            260                 265                 270
Asn Gln Trp Ala Lys Glu His Gly Val Asn Leu Ser Gln Tyr Val Lys
            275                 280                 285
Lys Ala Ser Arg Met Gly Asp Tyr Leu Arg Tyr Ala Met Phe Asp Lys
            290                 295                 300
Tyr Phe Arg Lys Ile Gly Asp Ser Lys Gln Ala Gly Thr Gly Tyr Asp
305                 310                 315                 320
Ala Ala His Tyr Leu Leu Ser Trp Tyr Ala Trp Gly Gly Ile
                325                 330                 335
Thr Ala Asp Trp Ala Trp Ile Ile Gly Cys Ser His Val His Ala Gly
            340                 345                 350
Tyr Gln Asn Pro Met Thr Ala Trp Ile Leu Ala Asn Asp Pro Glu Phe
            355                 360                 365
Lys Pro Glu Ser Pro Asn Gly Ala Asn Asp Trp Ala Lys Ser Leu Glu
            370                 375                 380
Arg Gln Leu Glu Phe Tyr Gln Trp Leu Gln Ser Ala Glu Gly Ala Ile
385                 390                 395                 400
Ala Gly Gly Ala Thr Asn Ser Tyr Lys Gly Arg Tyr Glu Thr Leu Pro
                405                 410                 415
Ala Gly Ile Ser Thr Phe Tyr Gly Met Ala Tyr Glu Glu His Pro Val
            420                 425                 430
Tyr Leu Asp Pro Gly Ser Asn Thr Trp Phe Gly Phe Gln Ala Trp Thr
            435                 440                 445
Met Gln Arg Val Ala Glu Tyr Tyr Leu Thr Gly Asp Thr Arg Ala
            450                 455                 460
Glu Gln Leu Leu Asp Lys Trp Val Asp Trp Ile Lys Ser Val Val Arg
465                 470                 475                 480
Leu Asn Ser Asp Gly Thr Phe Glu Ile Pro Gly Asn Leu Glu Trp Ser
                485                 490                 495
Gly Gln Pro Asp Thr Trp Thr Gly Thr Tyr Thr Gly Asn Pro Asn Leu
            500                 505                 510
His Val Ser Val Val Ser Tyr Gly Thr Asp Leu Gly Ala Ala Gly Ser
            515                 520                 525
Leu Ala Asn Ala Leu Leu Tyr Tyr Ala Lys Thr Ser Gly Asp Asp Glu
            530                 535                 540
Ala Arg Asn Leu Ala Lys Glu Leu Leu Asp Arg Met Trp Asn Leu Tyr
545                 550                 555                 560
Arg Asp Asp Lys Gly Leu Ser Ala Pro Glu Thr Arg Glu Asp Tyr Val
                565                 570                 575
Arg Phe Phe Glu Gln Glu Val Tyr Val Pro Gln Gly Trp Ser Gly Thr
            580                 585                 590
Met Pro Asn Gly Asp Arg Ile Glu Pro Gly Val Thr Phe Leu Asp Ile
            595                 600                 605
Arg Ser Lys Tyr Leu Asn Asp Pro Asp Tyr Pro Lys Leu Gln Gln Ala
610                 615                 620
Tyr Asn Glu Gly Lys Ala Pro Val Phe Asn Tyr His Arg Phe Trp Ala
625                 630                 635                 640
Gln Cys Asp Ile Ala Ile Ala Asn Gly Leu Tyr Ser Ile Leu Phe Gly
                645                 650                 655
Ser Glu Gln Ala Asn Asp Ser Phe Ile Thr Pro Thr Ser Ala Thr Phe
            660                 665                 670
```

-continued

```
Asp Lys Asn Asn Gln Glu Asp Ile Ser Val Thr Val Thr Tyr Asn Gly
        675                 680                 685

Asn Thr Leu Leu Gly Ile Lys Ser Gly Ser Ser Tyr Leu Ile Glu Gly
        690                 695                 700

Val Asp Tyr Ile Val Asn Gly Asp Val Ile Ile Lys Lys Glu Phe
705                 710                 715                 720

Leu Ala Gly Gln Ala Thr Gly Ser Ile Ser Leu Leu Phe Asp Phe Ser
                725                 730                 735

Ala Gly Leu Asp Arg Thr Leu Thr Ile Asp Ile Ile Asp Thr Gly Gly
                740                 745                 750

Gly Glu Glu Pro Val Glu Pro Val Glu Pro Val Glu Gly Val Leu Ile
                755                 760                 765

Ile Gln Ser Phe Asn Ala Asn Thr Gln Glu Ile Ser Asn Ser Ile Met
        770                 775                 780

Pro Arg Phe Arg Ile Tyr Asn Ser Gly Asn Thr Ser Ile Pro Leu Ser
785                 790                 795                 800

Glu Val Lys Leu Arg Tyr Tyr Tyr Thr Val Asp Gly Asp Lys Pro Gln
                805                 810                 815

Asn Phe Trp Cys Asp Trp Ala Ser Ile Gly Ser Ser Asn Val Thr Gly
                820                 825                 830

Thr Phe Val Lys Met Asp Gly Ala Thr Thr Gly Ala Asp Tyr Tyr Leu
                835                 840                 845

Glu Ile Gly Phe Thr Pro Gln Ala Gly Thr Leu Glu Pro Gly Ala Ser
        850                 855                 860

Ile Glu Val Gln Gly Arg Phe Ser Lys Ile Asp Trp Thr Asp Tyr Thr
865                 870                 875                 880

Gln Thr Asn Asp Tyr Ser Phe Asn Pro Thr Ala Ser Ser Tyr Val Asp
                885                 890                 895

Phe Asn Lys Ile Thr Ala Tyr Ile Ser Gly Asn Leu Val Tyr Gly Ile
                900                 905                 910

Glu Pro
```